US011064947B2

(12) United States Patent
Kang et al.

(10) Patent No.: US 11,064,947 B2
(45) Date of Patent: Jul. 20, 2021

(54) APPARATUS AND METHOD FOR MEASURING BIOMETRIC INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Seung Woo Noh, Seongnam-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 392 days.

(21) Appl. No.: 15/840,131

(22) Filed: Dec. 13, 2017

(65) Prior Publication Data

US 2019/0029596 A1 Jan. 31, 2019

(30) Foreign Application Priority Data

Jul. 25, 2017 (KR) .................. 10-2017-0094309

(51) Int. Cl.
*A61B 5/024* (2006.01)
*A61B 5/00* (2006.01)
(Continued)

(52) U.S. Cl.
CPC ........ *A61B 5/6843* (2013.01); *A61B 5/02007* (2013.01); *A61B 5/02108* (2013.01); *A61B 5/02116* (2013.01); *A61B 5/02225* (2013.01); *A61B 5/02416* (2013.01); *A61B 5/165* (2013.01); *A61B 5/4884* (2013.01); *A61B 5/681* (2013.01); *A61B 5/6824* (2013.01);
(Continued)

(58) Field of Classification Search
CPC ............ A61B 5/02108; A61B 5/02116; A61B 5/02416; A61B 5/681; A61B 5/6824; A61B 2090/065
See application file for complete search history.

(56) References Cited

U.S. PATENT DOCUMENTS 5,778,879 A * 7/1998 Ota .................... A61B 5/022
600/310
8,313,439 B2 11/2012 McCombie et al.
(Continued)

FOREIGN PATENT DOCUMENTS

EP      2 823 759 A1    1/2015
JP      2016-25935 A    2/2016
(Continued)

OTHER PUBLICATIONS

Communication dated Sep. 7, 2018, issued by the European Patent Office in counterpart European Application No. 18160950.4.
(Continued)

Primary Examiner — Puya Agahi
(74) Attorney, Agent, or Firm — Sughrue Mion, PLLC

(57) ABSTRACT

An apparatus for measuring biometric information is provided. The apparatus may include: a main body configured to be worn on an object to be examined. The main body may include a contact pressure sensor configured to measure a contact pressure of the object while a hand shape is changing; a pulse wave sensor configured to measure a pulse wave signal of the object; and a processor configured to measure biometric information on the basis of the measured contact pressure and pulse wave signal.

20 Claims, 15 Drawing Sheets

(51) Int. Cl.
*A61B 5/021* (2006.01)
*G06F 1/16* (2006.01)
*G06F 3/01* (2006.01)
*A61B 5/02* (2006.01)
*A61B 5/022* (2006.01)
*A61B 5/16* (2006.01)
*A61B 90/00* (2016.01)

(52) U.S. Cl.
CPC ............ *A61B 5/6831* (2013.01); *A61B 5/725* (2013.01); *A61B 5/7278* (2013.01); *A61B 5/743* (2013.01); *G06F 1/163* (2013.01); *G06F 3/015* (2013.01); *G06F 3/017* (2013.01); *A61B 5/7214* (2013.01); *A61B 2090/065* (2016.02); *A61B 2562/0247* (2013.01); *A61B 2562/0261* (2013.01)

(56) References Cited

U.S. PATENT DOCUMENTS

| | | | |
|---|---|---|---|
| 8,343,062 B2 | 1/2013 | Fortin et al. | |
| 8,721,557 B2 | 5/2014 | Chen et al. | |
| 8,798,703 B2 | 8/2014 | Huber et al. | |
| 8,814,800 B2 | 8/2014 | Fortin et al. | |
| 9,474,453 B2 | 10/2016 | Schnall | |
| 2007/0287923 A1 | 12/2007 | Adkins et al. | |
| 2008/0064967 A1 | 3/2008 | Ide | |
| 2008/0214942 A1 | 9/2008 | Oh et al. | |
| 2010/0130876 A1 | 5/2010 | Cho | |
| 2010/0241011 A1* | 9/2010 | McCombie | A61B 5/021 600/485 |
| 2011/0237963 A1* | 9/2011 | Nishioka | A61B 5/022 600/493 |
| 2014/0257050 A1* | 9/2014 | Kuroda | A61B 5/1116 600/301 |
| 2014/0276145 A1 | 9/2014 | Banet et al. | |
| 2015/0046095 A1 | 2/2015 | Takahashi et al. | |
| 2015/0182147 A1* | 7/2015 | Sato | A61B 5/02108 600/493 |
| 2016/0089081 A1 | 3/2016 | Morris et al. | |
| 2016/0091980 A1* | 3/2016 | Baranski | G06F 3/014 345/156 |
| 2016/0287102 A1 | 10/2016 | Saponas et al. | |
| 2017/0095171 A1* | 4/2017 | Park | A61B 5/02438 |
| 2018/0192946 A1* | 7/2018 | Adachi | A61B 5/022 |
| 2018/0353089 A1 | 12/2018 | Choi et al. | |

FOREIGN PATENT DOCUMENTS

| | | |
|---|---|---|
| KR | 10-2006-0081178 A | 7/2006 |
| KR | 10-2009-0052442 A | 5/2009 |
| KR | 10-2012-0108575 A | 10/2012 |
| KR | 10-2014-0050787 A | 4/2014 |
| KR | 10-2017-0067131 A | 6/2017 |
| WO | 2016161225 A1 | 10/2016 |

OTHER PUBLICATIONS

Office Action dated Sep. 20, 2019 by the European Patent Office in counterpart European Patent Application No. 18160950.4.

* cited by examiner

APPARATUS AND METHOD FOR MEASURING BIOMETRIC INFORMATION

CROSS-REFERENCE TO RELATED APPLICATION(S)

This application claims priority under 35 USC § 119(a) of Korean Patent Application No. 10-2017-0094309, filed on Jul. 25, 2017, in the Korean Intellectual Property Office, the entire disclosure of which is incorporated herein by reference for all purposes.

BACKGROUND

1. Field

Apparatuses and methods consistent with exemplary embodiments related to an apparatus and method for measuring biometric information, and particularly, to technology for measuring blood pressure while being worn on a wrist without a cuff.

2. Description of Related Art

Generally, methods of non-invasively measuring blood pressure without damaging the human body include a method of measuring blood pressure by measuring a cuff-based pressure itself and a method of estimating blood pressure by measuring a pulse wave without the use of a cuff.

A Korotkoff-sound method and an oscillometric method are used to measure the cuff-based blood pressure. According to the Korotkoff-sound method, a cuff is wound around an upper arm, a pressure in the cuff is increased, and blood pressure is measured by listening to the sound generated in the blood vessel through a stethoscope while decreasing the pressure. Since the Korotkoff-sound method requires a high level of proficiency from a measurer and the point at which the sound is heard may be different from one measurer to another due to different perceptions of hearing, blood pressure may be measured differently depending on the measurer.

The oscillometric method uses an automated machine to wrap a cuff around the upper arm, increase a cuff pressure, gradually measure a pressure in the cuff while gradually decreasing the cuff pressure, and measure blood pressure based on a point at which a change in the pressure signal is large. Since the oscillometric method requires that a strong pressure is applied to the cuff, repeated measurements may cause damage to blood vessels or tissues in patients with hypertension or in elderly people with less tissue elasticity. Further, most of the equipment is bulky, so it is not easy for individuals to measure the blood pressure while carrying the equipment.

Cuffless blood pressure measurement methods generally include a method of measuring blood pressure by calculating a pulse transit time (PTT) and a pulse wave analysis (PWA) method of estimating blood pressure by analyzing the shape of a pulse wave. The PTT and the shape of a pulse wave are caused by various factors, other than blood pressure, and thus these methods have limited accuracy.

SUMMARY

This summary is provided to introduce a selection of concepts in a simplified form that are further described below in the Detailed Description. This summary is not intended to identify key features or essential features of exemplary embodiments.

According to an aspect of an exemplary embodiment, there is provided an apparatus for measuring biometric information including: a main body configured to be worn on an object to be examined; a contact pressure sensor mounted in the main body and configured to measure a contact pressure of the object while a hand shape is changing; a pulse wave sensor mounted in the main body and configured to measure a pulse wave signal of the object; and a processor mounted in the main body and configured to measure biometric information on the basis of the measured contact pressure and pulse wave signal.

The apparatus may further include a strap connected to both ends of the main body and configured to fix the main body to the object while wrapping around the object.

The contact pressure sensor may include a force sensor or a strain gauge for measuring the contact pressure of the object transmitted through the main body while the hand shape is changing.

The pulse wave sensor may include one or more light sources configured to emit light to the object and one or more detectors configured to detect light scattered or reflected from the object which is irradiated by the one or more light sources.

The one or more light sources may include at least one of a light emitting diode (LED), a laser diode, and a fluorescent body.

The apparatus may further include an outputter mounted in the main body and configured to output guidance information for a motion to change the hand shape when a request for measuring biometric information is received.

The motion to change the hand shape may include at least one of a motion of extending at least one finger from a fist, a motion of making a fist in a state in which at least one finger is unfolded, a motion of sequentially opening each finger from a fist, and a motion of sequentially curling stretched fingers of an open hand, one by one, into a fist.

The motion to change the hand shape may include at least one of a motion of bending a wrist in one direction in a state holding a fist or in a state keeping at least one finger unfolded, a motion of squeezing fingers while holding a fist, a motion of stretching at least two unfolded fingers apart from each other, a motion of bending a palm downward or backward with all fingers open, and a motion of pressing the main body with a hand on which the main body is not worn.

When the processor measures the biometric information, the outputter may output a measurement result.

The apparatus may further include a storage unit mounted in the main body and configured to store at least one of guidance information for a motion to change the hand shape and the measurement result of the biometric information.

The processor may extract feature points on the basis of the measured pulse wave signal and a contact pressure signal and measure the biometric information using the extracted feature point and a measurement model.

The processor may generate a contact pressure versus pulse wave graph on the basis of the contact pressure signal and the pulse wave signal, and extract at least one of a contact pressure value and a pulse wave value at a maximum peak of the generated graph.

The biometric information may include at least one of systolic blood pressure, diastolic blood pressure, vascular age, arterial stiffness, aortic artery pressure waveform, vascular elasticity, stress index, and fatigue level.

According to an aspect of another exemplary embodiment, there is provided a method of measuring biometric information including: measuring a contact pressure of an object to be examined while a handshape is changing; measuring a pulse wave signal of the object; and measuring biometric information on the basis of the measured contact pressure and pulse wave signal.

The method may further include: receiving a request for measuring biometric information; and outputting guidance information for a motion to change the hand shape when the request for measuring biometric information is received.

The motion to change the hand shape may include at least one of a motion of extending at least one finger from a fist, a motion of making a fist in a state in which at least one finger is unfolded, a motion of sequentially opening each finger from a fist, and a motion of sequentially curling stretched fingers of an open hand, one by one, into a fist.

The motion to change the hand shape may include at least one of a motion of bending a wrist in one direction in a state holding a fist or in a state keeping at least one finger unfolded, a motion of squeezing fingers while holding a fist, a motion of stretching at least two unfolded fingers to be apart from each other, a motion of bending a palm downward or backward with all fingers open, and a motion of pressing the main body with a hand on which the main body is not worn.

The method may further include, when the biometric information is measured, outputting a measurement result.

The measuring of the biometric information may include extracting feature points on the basis of the measured pulse wave signal and a contact pressure signal and measuring the biometric information using the extracted feature point and a measurement model.

According to an aspect of another exemplary embodiment, there is provided an apparatus for measuring biometric information including: a main body configured to be worn on an object to be examined; a contact pressure sensor mounted in the main body and configured to measure a contact pressure of the object while a hand shape is changing; a pulse wave sensor mounted in the main body and configured to measure a pulse wave signal of the object; a processor mounted in the main body and configured to measure biometric information on the basis of the measured contact pressure and pulse wave signal; and a communicator mounted in the main body and configured to communicate with an external device under a control of the processor.

The apparatus may further include an outputter mounted in the main body and configured to output at least one of guidance information for a motion to change the hand shape and measurement result of the biometric information.

The processor may control the outputter to output the guidance information or controls the communicator to transmit and output the guidance information to the external device when a request for measuring biometric information is received.

The processor may determine whether to correct a measurement model for measuring the biometric information, control the communicator to receive reference data from the external device when it is determined that the measurement model is needed to be corrected, and correct the measurement model on the basis of the reference data.

The reference data may include at least one of cuff blood pressure data and cuff pressure data measured by a cuff-type blood pressure measuring device.

The measurement model may be constructed in a form of a linear function or a mapping table which represents a correlation between the biometric information and feature points extracted on the basis of the contact pressure and the pulse wave signal.

According to an aspect of another exemplary embodiment, there is provided an apparatus for measuring biometric information including: a main body configured to be worn on an object to be examined; a strap configured to wrap around the object and fix the main body to the object; a pressure sensor mounted in the main body and configured to measure a pressure signal transmitted through the strap while a hand shape is changing; and a processor mounted in the main body and configured to measure biometric information on the basis of the measured pressure signal.

The strap may have one end connected to the pressure sensor and may be shaped as a cuff into which air is injected.

The pressure sensor may measure a pressure signal generated when the strap pressurizes or depressurizes the object according to the change of the hand shape.

The processor may measure blood pressure of the object using an oscillometric method on the basis of the measured pressure signal.

The processor may pass the measured pressure signal through a low pass filter (LPF) and a bandpass filter (BPF) to respectively extract pressure data and a pulse wave signal, and measure the blood pressure on the basis of the extracted pressure data and pulse wave signal.

The apparatus may further include an outputter mounted in the main body and configured to output guidance information for a motion to change the hand shape when a request for measuring biometric information is received.

Other exemplary features and aspects will be apparent from the following detailed description and the drawings.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

Figure 1A:
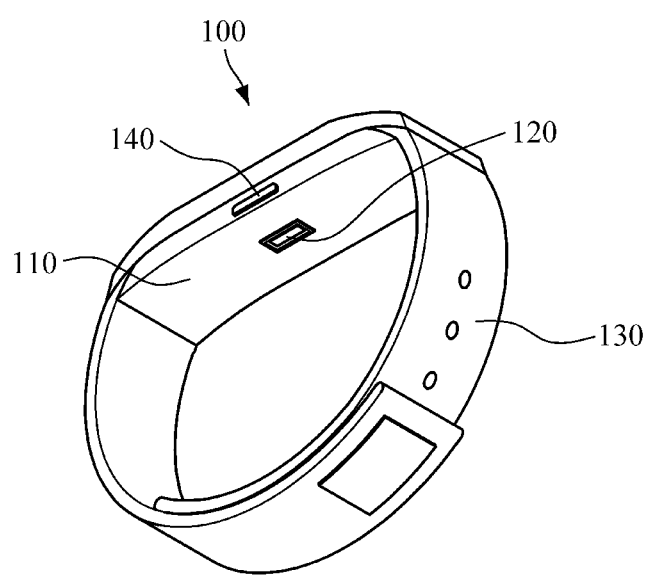
FIG. 1A is a diagram illustrating a configuration of an apparatus for measuring biometric information according to an exemplary embodiment

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Exemplary advantages and features and methods of accomplishing the same may be understood more readily by reference to the following detailed description of exemplary embodiments and the accompanying drawings. The exemplary embodiments should not be construed as limiting, and modifications may be made thereto. Rather, these exemplary embodiments are provided so that this disclosure will be thorough and complete. Like reference numerals refer to like elements throughout the specification.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as " . . . unit" and "module" denote units that process at least one function or operation, and they may be implemented by using hardware, software, or a combination of hardware and software.

Hereinafter, exemplary embodiments of an apparatus and method for measuring biometric information will be described in detail with reference to the accompanying drawings.

Figure 1B:
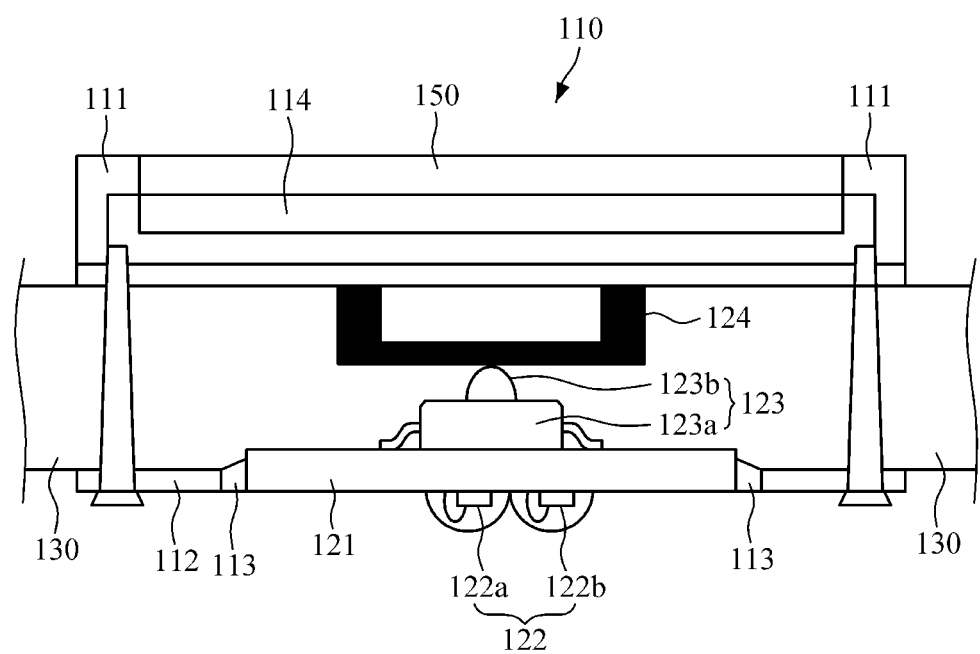
FIG. 1B is a cross-sectional diagram of a main body 110 of the apparatus of FIG. 1A.

FIG. 1A is a diagram illustrating an apparatus for measuring biometric information according to an exemplary embodiment. FIG. 1B is a diagram schematically illustrating a configuration of a main body 110 of the apparatus for measuring biometric information according to an exemplary embodiment.

Referring to FIG. 1A, an apparatus 100 for measuring biometric information may be a wearable device which may be worn on a wrist. The apparatus 100 includes a main body 110 to be worn on an object to be examined and a strap connected to both ends of the main body 110 and configured to secure the main body 110 to the object by wrapping around the object by tension.

Modules related to biometric information measurement and modules related to additional functions (e.g., watch, alarm, music player, movie player, etc.) may be mounted in the main body 110 of the apparatus 100. For example, as shown in FIG. 1A, the main body 110 may be provided with a sensor 120 including a contact pressure sensor or a pulse wave sensor necessary for measuring biometric information. In addition, an operator 140 configured to receive various control commands of a user may be mounted in the main body 110. In this case, the operator 140 may include a power button function, which enables the user to input a power on/off command for the apparatus 100. In addition, although not illustrated, the main body 110 may be provided with a display for visually providing a variety of information, or a speaker or a haptic device for non-visually providing the information.

Referring to FIG. 1B, a configuration of the main body 110 of the apparatus 100 according to an exemplary embodiment may include a sensor board 121, connected at both ends to a housing 112, and a main board 114 supported by a cover 111.

The pulse wave sensor 122 may be mounted on one surface of the sensor board 121 so as to be exposed toward the object, and the contact pressure sensor 123 may be mounted on an opposite surface of the sensor board 121 so as to face the inside of the housing 112. In this case, one or more connection portions 113, disposed between the sensor board 121 and the housing 112, may be expandable and contractible. The connection portion 113 enables a movement of the sensor board 121 when a pressure applied from the object, for example, a wrist of the user, is transmitted to the housing 112 of the main body 110 by the tension of the strap 130 as the user changes a shape of a hand.

The pulse wave sensor 122 may measure a photoplethysmography (PPG) signal (hereinafter, referred to as a "pulse wave signal"). In this case, the object may be an upper part of a wrist of the user, through which venous blood vessels or capillaries pass, but is not limited thereto, and it may be a region of a lower part of the wrist of the user, through which the radial artery passes. The pulse wave sensor 122, as shown in FIG. 1B, may include one or more light sources 122a configured to emit light to the object and one or more detectors 122b configured to detect light scattered or reflected from the object which is irradiated by the light sources 122a. In this case, the light sources 122a may include a light emitting diode (LED), a laser diode, and a fluorescent body, but are not limited thereto.

The contact pressure sensor 123 may include a force sensor 123a, with appropriate sensitivity, and a pressurizing member 123b. However, the type of the contact pressure sensor 123 is not limited to the above examples, and it is apparent that various sensors, such as a strain gauge and the like, for measuring a contact pressure may be provided. When the user changes a shape of the hand, the muscles of the wrist are contracted or relaxed and the thickness of the wrist changes accordingly. When the thickness of the wrist is changed, the sensor board 121 is caused to move by the tension of the strap which wraps around the wrist. The pressurizing member 123b of the contact pressure sensor 123 mounted on the sensor board 121 applies a pressure to a rigid support body 124 according to the movement of the sensor board 121, and the force sensor 123a of the contact pressure sensor 123 may measure a contact pressure signal which is generated as the pressurizing member 123b pressurizes the rigid support body 124.

The pulse wave sensor 122 or the contact pressures sensor 123 may be electrically connected to the sensor board 121. The pulse wave signal or the contact pressure signal measured by the pulse wave sensor 122 or the contact pressure sensor 123 may be transmitted to the main board 114 through the sensor board 121 electrically connected to the pulse wave sensor 122 or the contact pressure sensor 123. However, exemplary embodiments are not limited thereto, such that the pulse wave sensor 122 or the contact pressure sensor 123 may be directly electrically connected to the main board 114.

The main board 114 may be supported by the cover 111, and a display 150, configured to visually display a variety of information, may be provided on one surface of the main board 114. In addition, the main board 114 may be provided with a speaker module or a haptic module configured to output information non-visually. Also, the main board 114 may be provided with a processor configured to execute an algorithm for measuring biometric information or to control various modules. The main board 114 may be electrically connected to the sensor board 121 and receive the measured pulse wave signal or contact pressure signal, and the processor may measure biometric information on the basis of the received pulse wave signal or contact pressure signal.

Figure 2:
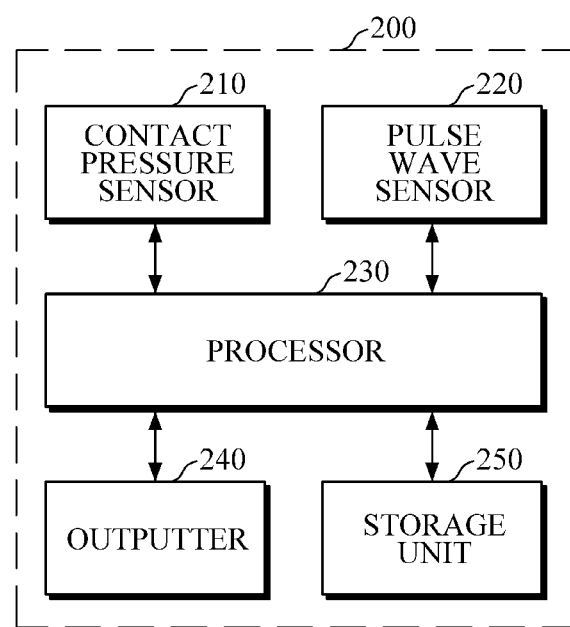
FIG. 2 is a block diagram illustrating an apparatus for measuring biometric information according to an exemplary embodiment.
Figure 3A:
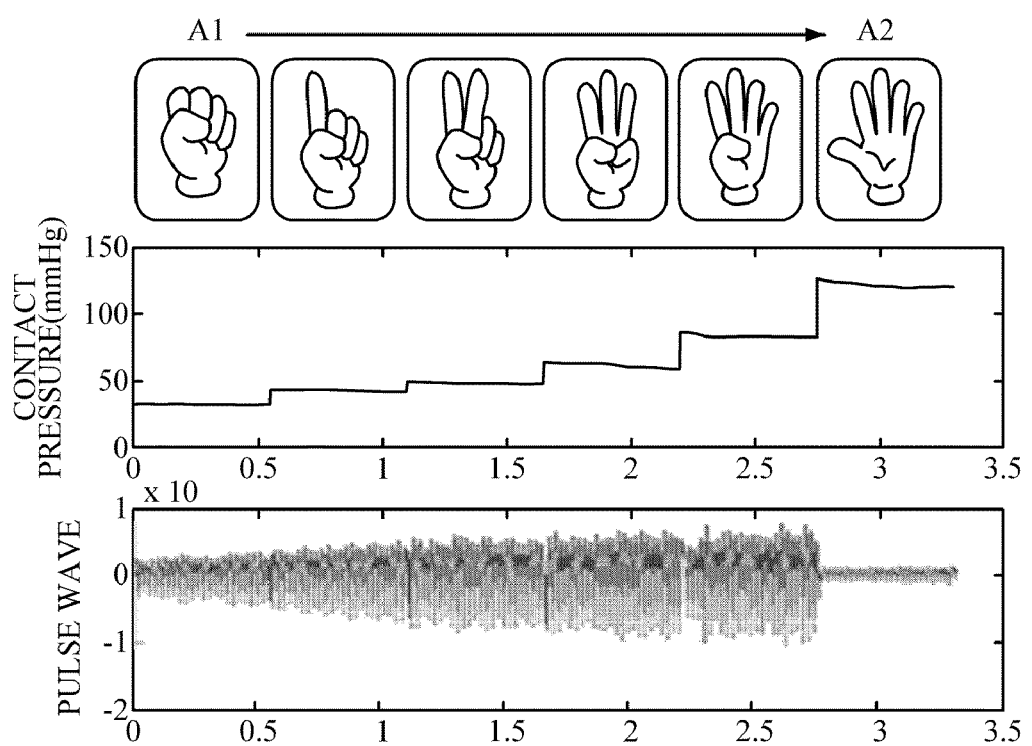
FIGS. 3A and 3B are diagrams illustrating exemplary embodiments of changes in contact pressure and pulse wave signal according to a change of a shape of a hand.
Figure 3B:
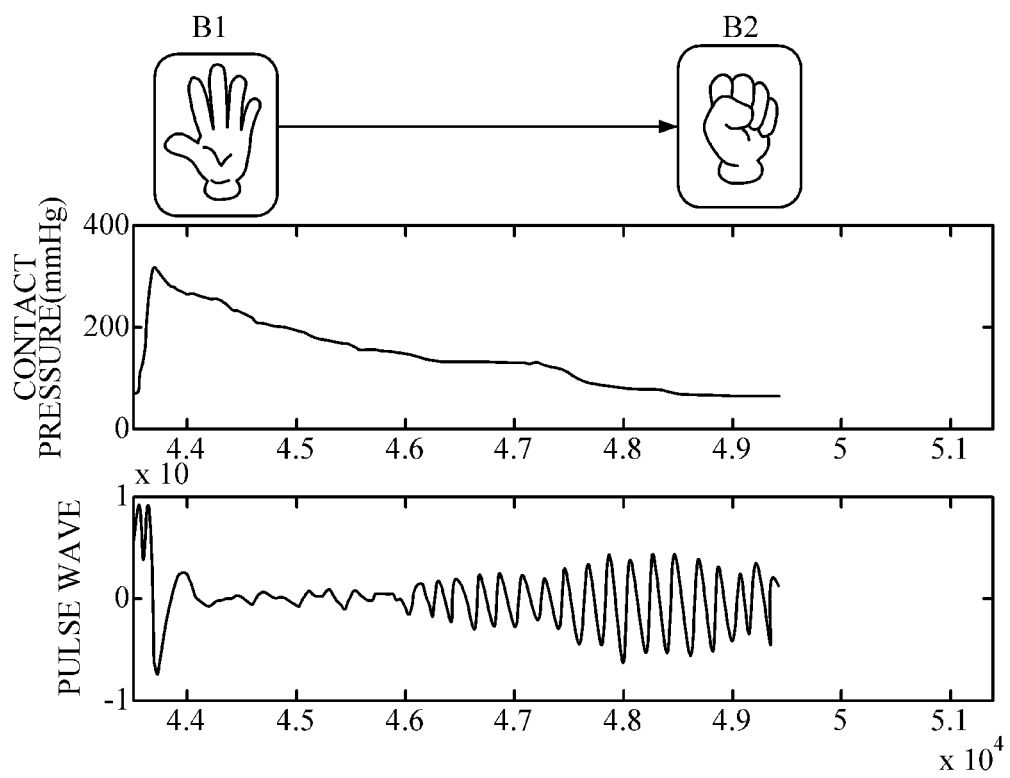

FIG. 2 is a block diagram illustrating an apparatus for measuring biometric information according to an exemplary embodiment. FIGS. 3A and 3B are diagrams illustrating embodiments of changes in contact pressure and pulse wave signal according to the change of the hand shape. FIGS. 4A to 4E are diagrams for describing examples of biometric information measurement according to an exemplary embodiment.

An exemplary embodiment in which an apparatus for measuring biometric information measures biometric information will be described with reference to FIGS. 2 to 4E. In this exemplary embodiment, the biometric information may include systolic blood pressure, diastolic blood pressure, vascular age, arterial stiffness, aortic artery pressure waveform, vascular elasticity, stress index, fatigue level, and the like, but is not limited thereto. Hereinafter, for convenience of description, an example in which the apparatus for measuring biometric information is worn on a wrist and measures a blood pressure will be described.

Referring to FIG. 2, an apparatus 200 for measuring biometric information includes a contact pressure sensor 210, a pulse wave sensor 220, a processor 230, an outputter 240, and a storage unit 250.

When the processor 230 receive a request for measuring biometric information, the processor 230 may control the outputter 240 to guide the user, using a visual and/or non-visual method, in motions to change the user's hand shape. The request for measuring biometric information may be input by the user through an interface provided on the operator or on the display. Alternatively, the processor 230 may check a pre-set measurement interval, which is stored in the storage unit 250, and may automatically generate a control command for measuring biometric information at the pre-set measurement intervals.

The processor 230 may display guidance information for the motions to change the hand shape. While the user changes the shape of the hand according to the guidance, the processor 230 may control the pulse wave sensor 220 and the contact pressure sensor 210 to measure a pulse wave signal and a contact pressure signal.

When the user who is wearing the main body on his/her wrist changes the hand shape according to the guidance, the thickness of the wrist changes as the muscles of the wrist are relaxed or contracted. The contact pressure sensor 210 may measure a change in pressure applied to the wrist by the tension of the strap wrapping the wrist according to the change of the hand shape. In addition, the pulse wave sensor 220 may simultaneously measure change in a pulse wave signal in an examination region of the wrist, such as venous blood vessels, capillaries, or radial artery, according to the change of the hand shape.

When the pulse wave sensor 210 and the contact pressure sensor 220 measure the pulse wave signal and the contact pressure signal, respectively, the processor 230 may receive the measured pulse wave signal and contact pressure signal. The processor 230 may store the received pulse wave signal and contact pressure signal in the storage unit 250. In addition, the processor 230 may measure the user's blood pressure on the basis of the received pulse wave signal and contact pressure signal.

When the received pulse wave signal and contact pressure signal are determined to be insufficient for measuring the blood pressure or when the measured blood pressure is determined to be abnormal, for example, when the measured blood pressure is outside of a normal blood pressure range which is pre-set for a specific user, the processor 230 may determine to re-measure a contact pressure signal and a pulse wave signal. In this case, the processor 230 may guide the user in another motion different than the previously guided motion to change the hand shape.

The outputter 240 may include a display configured to visually display information or an output module configured to output the information through a non-visual method. In this case, examples of a non-visual output module may include a speaker module configured to audibly output information and a haptic module configured to output information through vibration or tactile sensation. The outputter 240 may output a blood pressure measurement result or the measured pulse wave signal or contact pressure signal under the control of the processor 230. The processor 230 may determine an output method suitable for the user on the basis of user characteristic information, such as the user's sex, age, health condition, or the like, and control the module of the outputter 240 corresponding to the determined output method to output the information.

A plurality of motions for changing the user's hand shape, guidance information for specific motions suitable for the user's characteristics among the plurality of motions, reference information, such as a measurement model for biometric information measurement, and measurement results may be stored in the storage unit 250. The storage unit 250 may include a storage medium, such as a flash memory type memory, a hard disk type memory, a multimedia card micro type memory, a card-type memory (e.g., secure digital (SD) or extreme digital (XD) memory, etc.) random access memory (RAM), static random access memory (SRAM), read-only memory (ROM), electrically erasable programmable read-only memory (EEPROM), programmable read-only memory, magnetic memory, magnetic disk, and optical disk, but is not limited thereto.

FIGS. 3A and 3B are diagrams illustrating user's hand shape and a contact pressure and pulse wave signal measured according to the change of hand shape.

FIG. 3A illustrates an example in which, according to guidance of the processor 230, a user holds his/her hand in a fist A1 and unfolds each finger, one by one, at a predetermined time interval, for example, at an interval of 30 seconds, so that all fingers of the hand are extended (open hand A2).

Generally, since the thickness of the wrist is larger when the hand is open with all fingers extended than when the hand is held in a fist, a pressure exerted on the wrist by the strap increases gradually as the user changes the shape of hand from the fist A1 to the open hand A2 by unfolding each finger. Accordingly, as shown in the drawings, the contact pressure measured by the contact pressure sensor 210 increases gradually according to the change of the hand shape. In addition, according to the change of the hand shape, the envelope of the pulse wave signal measured at capillaries, venous blood vessels, or radial artery in the upper part of the wrist may also be change, and the pulse wave sensor 220 measures the changed pulse wave signal.

FIG. 3B is a diagram illustrating an example in which the user changes a hand shape from an open hand B1 with all fingers extended to a fist-holding hand B2 according to guidance of the processor 230. Since the shape of the hand is changed from the open hand with all fingers extended to a shape of a fist, the contact pressure measured by the contact pressure sensor 210 is the strongest when all fingers of the hand are extended, and it gradually decreases, as shown in the drawing. The pulse wave sensor 220 measures the pulse wave signal that changes according to the change of the hand shape.

However, the motions to change the hand shape are not limited to the examples shown in FIGS. 3A and 3B, and may include any motions causing a change in pressure exerted on the object, for example, a motion of extending at least one finger from a fist, a motion of making a fist in a state in which at least one finger is unfolded, a motion of sequentially curling the stretched fingers of the open hand, one by one, into a fist, a motion of bending a wrist in one direction in a state holding a fist or in a state keeping at least one finger unfolded, a motion of squeezing fingers while holding a fist, a motion of stretching at least two unfolded fingers apart from each other, a motion of bending a palm downward or backward with all fingers open, and a motion of pressing the main body with a hand on which the main body is not worn.

An exemplary embodiment in which the processor 230 measures a blood pressure will be described with reference to FIGS. 4A to 4E. For example, the processor 230 may measure a blood pressure on the basis of an oscillometric method.

The processor 230 may guide the user via the outputter 240 such that the user performs a motion to change a shape of the hand on which the main body is worn from a fist to an open hand with all fingers extended.

Figure 4A:
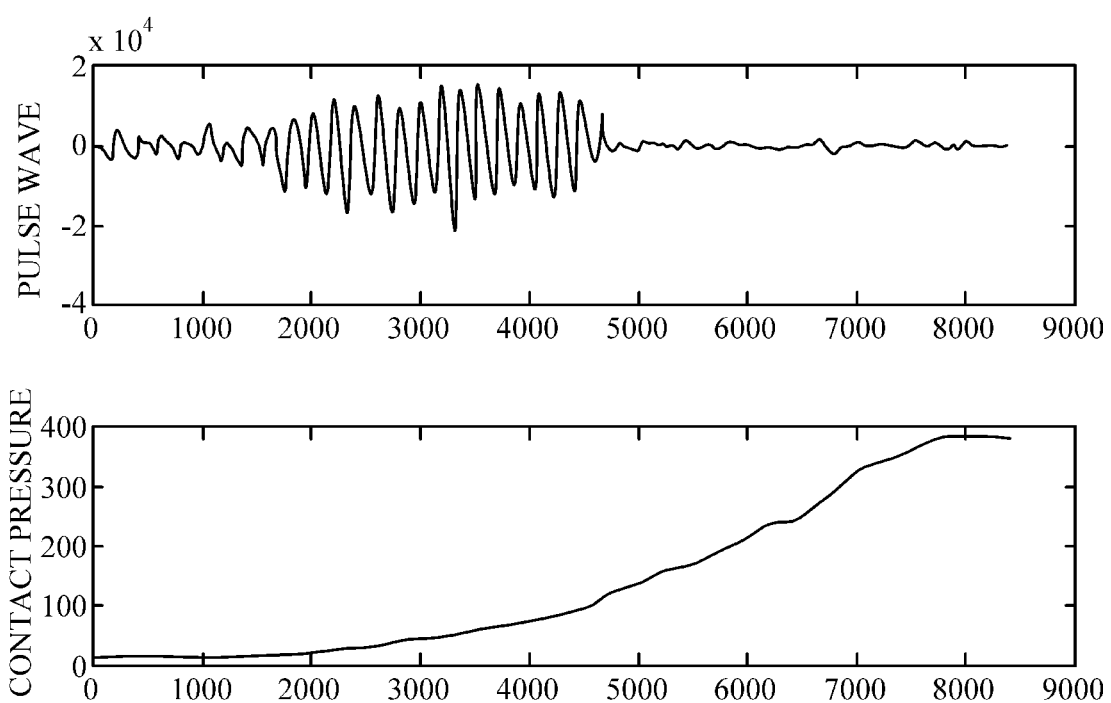
FIGS. 4A, 4B, 4C, 4D, and 4E are diagrams of exemplary biometric information measurement according to an exemplary embodiment.

The contact pressure sensor 210 and the pulse wave sensor 220 may measure a contact pressure signal and a pulse wave signal while the user is performing a motion to change the hand shape. In this case, since the thickness of the wrist gradually increases as the user changes the shape of the hand from the fist to the open hand with all fingers extended, the pressure exerted on the wrist by the tension of the strap wrapping around the wrist gradually increases. Therefore, the contact pressure of the object measured by the contact pressure sensor 210 gradually increases as shown in FIG. 4A. In addition, the envelope of the pulse wave signal measured by the pulse wave sensor 220 is also changed, as compared to when the pressure applied to the wrist does not change.

Figure 4B:
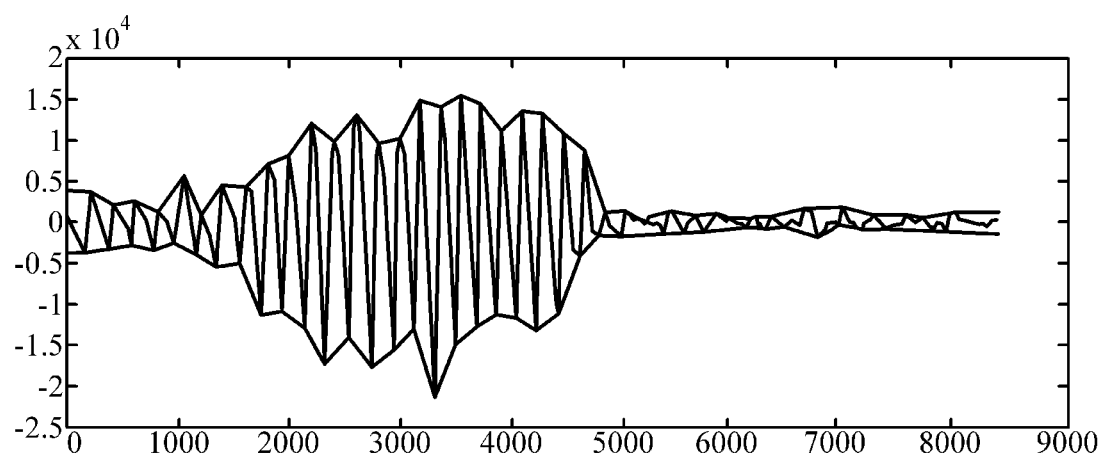
Figure 4C:
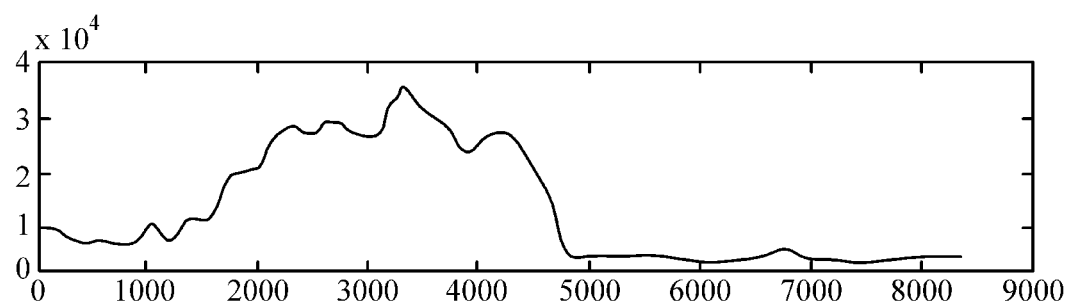

Then, when the contact pressure signal and the pulse wave signal are measured by the contact pressure sensor 210 and the pulse wave sensor 220, respectively, the processor 230 may obtain an envelope of a waveform from the measured pulse wave signal, as shown in FIG. 4B, and may use the obtained envelope of the pulse wave signal waveform to extract peak-to-peak points of the pulse wave signal waveform by subtracting a value on minus side from a value on positive side of a waveform at each time of measurement, as shown in FIG. 4C.

Figure 4D:
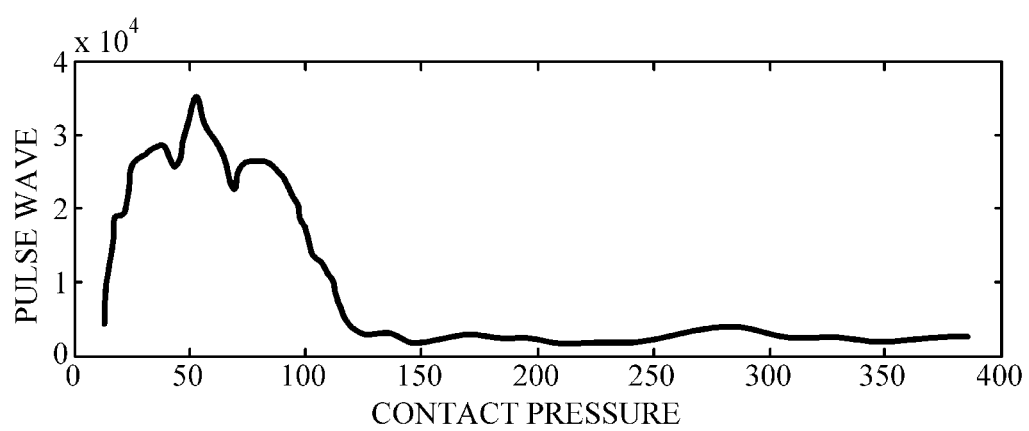

Then, as shown in FIG. 4D, the processor 230 may generate a contact pressure versus pulse wave graph by plotting the peak-to-peak points of pulse wave signal waveform of FIG. 4C with respect to a contact pressure value, extracted at the same measurement time point.

Then, the processor 230 may extract feature points using the contact pressure versus pulse wave graph generated in FIG. 4D and measure biometric information using the extracted feature points. In this case, the processor 230 may extract a contact pressure value, a pulse wave value, or the like at a point at which the maximum peak occurs in the contact pressure versus pulse wave graph as the feature point.

Figure 4E:
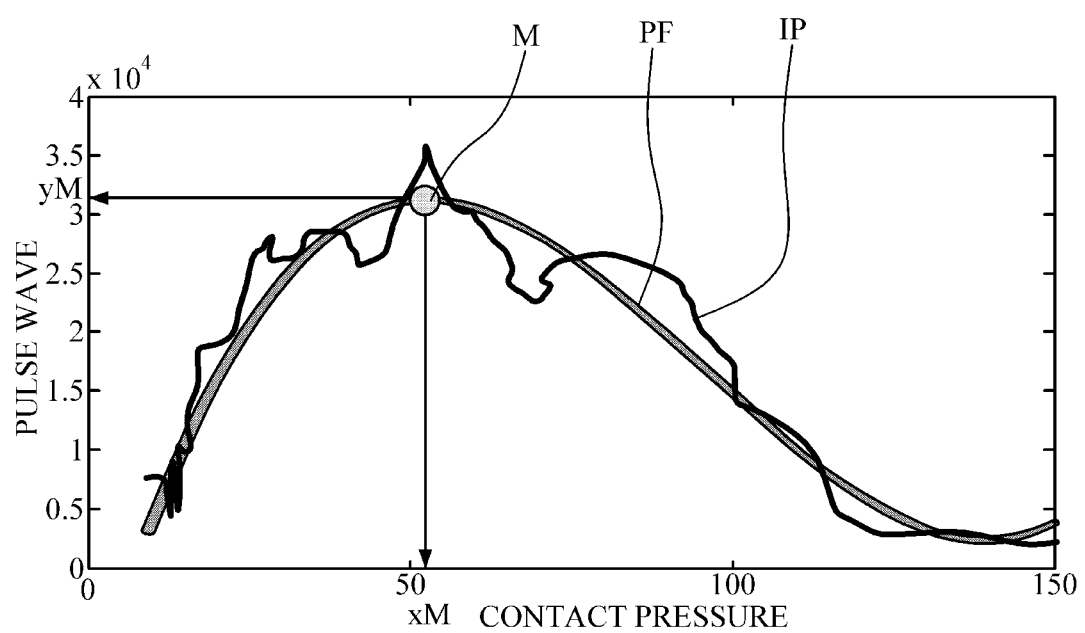

In one example, as shown in FIG. 4E, the processor 230 may perform $3^{rd}$-order polynomial fitting on the contact pressure versus pulse wave graph IP generated in FIG. 4D, and may extract a contact pressure value xM or a pulse wave yM at the maximum peak point M of a graph PF obtained as a result of the $3^{rd}$-order polynomial fitting as the feature point. The contact pressure value xM at a point where the maximum peak occurs may be extracted as the feature point for calculating a mean blood pressure (MBP) and contact pressure values at the right and left points which are symmetrically distant from the contact pressure value xM at the point where the maximum peak occurs and which have a peak at a pre-set ratio within a range from 0.5 to 0.7 may be extracted as feature points for calculating systolic blood pressure (SBP) and diastolic blood pressure (DBP).

Then, the processor 230 may obtain SBP, DBP, MBP, or the like by inputting the extracted feature point to a biometric information measurement model. In this case, the biometric information measurement model may be constructed in advance as a linear function as shown in Equation 1 below, but it is not limited thereto and may be constructed in the form of a table in which blood pressure values are mapped to feature points.

$$y=ax+b \qquad (1)$$

Here, y denotes biometric information to be obtained, i.e., SBP, DBP, MBP, and the like, and x denotes the extracted feature point. In addition, a and b are constant values obtained in advance through preprocessing and they may be defined differently according to the type of biometric information to be measured.

When the biometric information of interest is measured, the processor 230 may output a measurement result through the outputter 240. In this case, the outputter 240 may visually display the measurement result on a display or audibly provide the measurement result under the control of the processor 230. In addition, when the biometric information is measured, the processor 230 may determine whether the user's health condition is abnormal, and when it is determined that an abnormal condition occurs, the processor 230 may provide a warning or alarm information. For example, when measured blood pressure deviates from the user's usual blood pressure, the blood pressure value may be displayed in red, or a warning may be given via vibration through a haptic module. Alternatively, the processor 230 may audibly notify the user of the abnormal condition and guide the user for an action to take.

Figure 5:
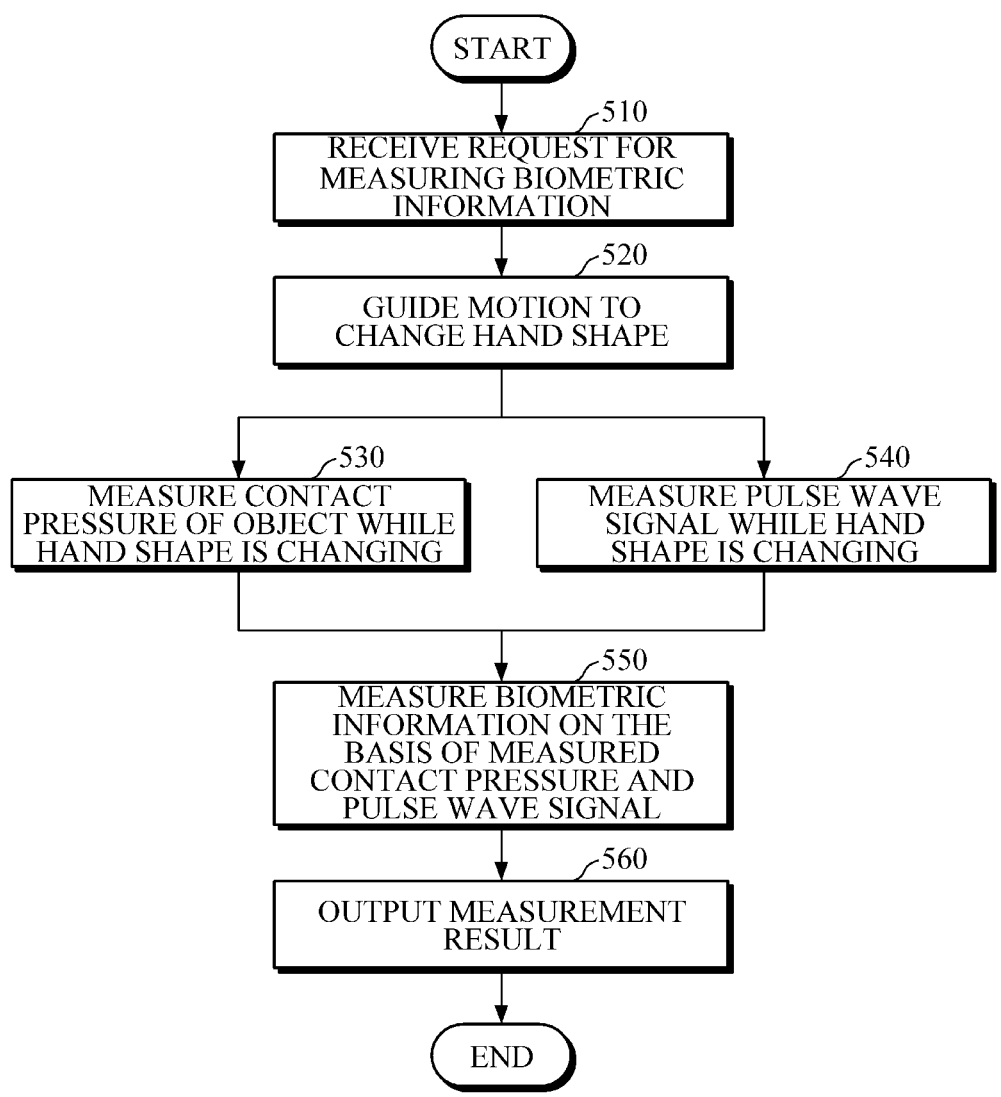
FIG. 5 is a flowchart illustrating a method of measuring biometric information according to an exemplary embodiment.

FIG. 5 is a flowchart illustrating a method of measuring biometric information according to an exemplary embodiment. The method of measuring biometric information shown in FIG. 5 may be performed by the above-described apparatus 200 for measuring biometric information, and it will be briefly described The apparatus 200 for measuring biometric information receives a request for measuring biometric information, as depicted in 510, and guides the user in a motion to change a hand shape, as depicted in 520. In this case, as described above, the motion to change the hand shape may include any of various motions to increase or decrease a pressure to be applied to the object through the strap wrapping around the object by relaxing or contracting the muscles of the object on which the main body is worn, for example, the wrist.

Then, the contact pressure sensor measures a contact pressure while the user performs the motion to change the hand shape, as depicted in 530, and concurrently, the pulse wave sensor emits light to the object and detects light scattered or reflected from the object to measure a pulse wave signal, as depicted in 540.

Then, biometric information is measured on the basis of the measured contact pressure and pulse wave signal, as depicted in 550. For example, when the contact pressure and the pulse wave signal are measured, the apparatus 200 may measure a blood pressure, which is one of biometric information, on the basis of an oscillometric method, as described above. In addition, the apparatus 200 may store the measured contact pressure signal, the measured pulse wave signal, and the measurement results in the storage unit.

Then, when the biometric information is measured, the measurement result may be provided to the user, as depicted in 560. When the biometric information is measured, the apparatus 200 may determine whether the user's health condition is problematic on the basis of the measurement result and may provide warning or alarm information to the user according to a determination result.

Figure 6:
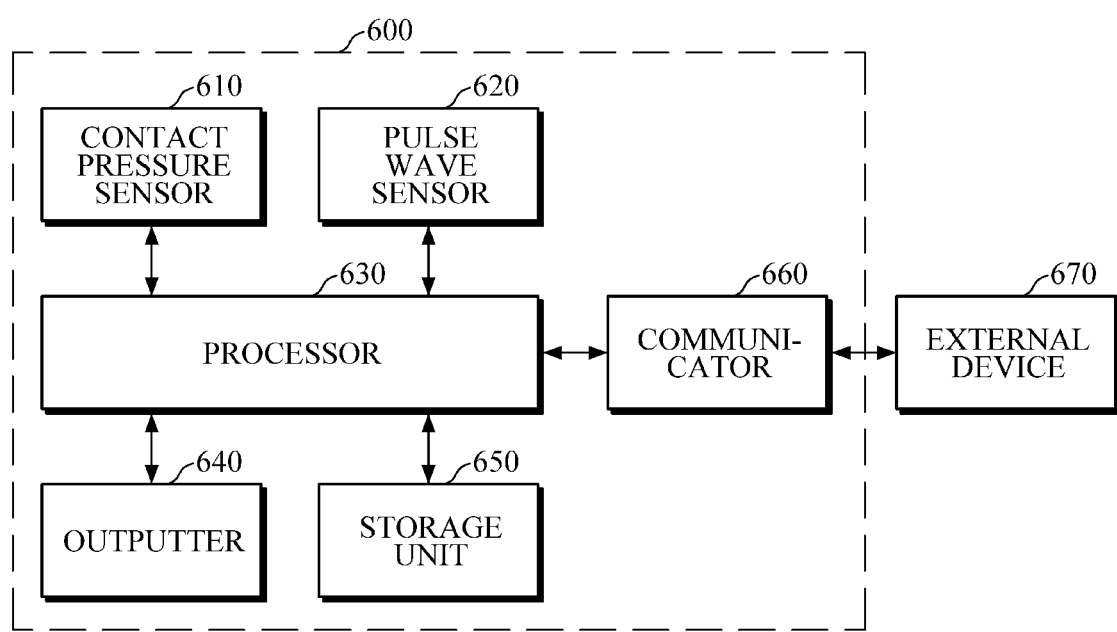
FIG. 6 is a block diagram illustrating an apparatus for measuring biometric information according to another exemplary embodiment.

FIG. 6 is a block diagram illustrating an apparatus for measuring biometric information according to another exemplary embodiment.

Referring to FIG. 6, an apparatus 600 for measuring biometric information includes a contact pressure sensor 610, a pulse wave sensor 620, a processor 630, an outputter 640, a storage unit 650, and a communicator 660. Some parts 610, 620, 630, 640, and 650 of the apparatus 600 according to the present exemplary embodiment perform basically the same functions as the parts 210, 220, 230, 240, and 250 in the exemplary embodiment described with reference to FIG. 2, and hence detailed descriptions thereof will be omitted.

When a request for measuring biometric information is received, the processor 630 may extract guidance information for a motion to change a user's hand shape from the storage unit 650 and provide the guidance information to the user through the outputter 640. In addition, the processor 630 may control the contact pressure sensor 610 and the pulse wave sensor 620 to measure a contact pressure and a pulse wave signal while the user performs a motion to change the hand shape according to the guidance information.

When the contact pressure signal and the pulse wave signal measured by the contact pressure sensor and the pulse wave sensor are received, the processor 640 may measure biometric information on the basis of the received contact pressure signal and pulse wave signal.

The processor 640 may control the communicator 660, which is connected with an external device 670, and may process various functions including functions needed for biometric information measurement through cooperation with the connected external device 670. In this case, the external device 670 may include a smartphone, a tablet personal computer (PC), a desktop PC, a notebook PC, a medical institution server, and a medical device, such as a cuff-type blood pressure measuring device.

The communicator 660 may connect with a communication network using a communication technology under the control of the processor 640. The communication technology includes Bluetooth communication, Bluetooth low energy (BLE) communication, near field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like, but is not limited thereto.

For example, the processor 640 may determine whether to correct data necessary for measuring biometric information. When it is determined that correction is needed, the processor 640 controls the communicator 660 to establish a connection with the external device 670. In this case, at a pre-set interval, or when the measured value of biometric information does not satisfy a predetermined criterion, the processor 640 may determine that correction of a biometric information measurement model for measuring biometric information is needed.

In addition, when the communicator 660 is connected to the external device 670 and receives reference data for correction of, for example, a biometric information measurement model, the processor 630 may correct the biometric information measurement model using the received reference data. The processor 630 may store the received reference data and/or the corrected measurement model in the storage unit 650. If the biometric information to be measured is blood pressure, the external device 670 may be a cuff-type blood pressure measuring device, and the received reference data may include a cuff-pressure and user's cuff blood pressure measured by use of the cuff-type blood pressure measuring device. However, the received data is not limited to the above examples, and the measurement model itself, which is periodically updated for the user at a medical institution, may be received as the reference data.

In another example, when the contact pressure signal and the pulse wave signal are measured, the processor 630 may transmit the measured contact pressure signal and pulse wave signal to the external device 670, allowing the external device 670, having a relatively excellent processing performance, to measure the biometric information. In this case, the external device 670 may be a smartphone or tablet PC carried by the user, a desktop PC or notebook PC of the user, a medical institution server for managing the user's health condition, or the like. The external device 670 may employ a biometric information measurement algorithm, for example, an algorithm that measures blood pressure on the basis of an oscillometric method.

In another example, the processor 630 may transmit the measured biometric information to the external device 670, having a relatively excellent computing performance, such as memory performance, display performance, or the like, compared to the apparatus 600 for measuring biometric information, and may allow the external device 670 to manage a history of biometric information measurement. In addition, the processor 630 may provide the measurement result to the user through the outputter 640, or may provide the measured biometric information, biometric information history information, and other additional information to the user through the external device 670.

Figure 7:
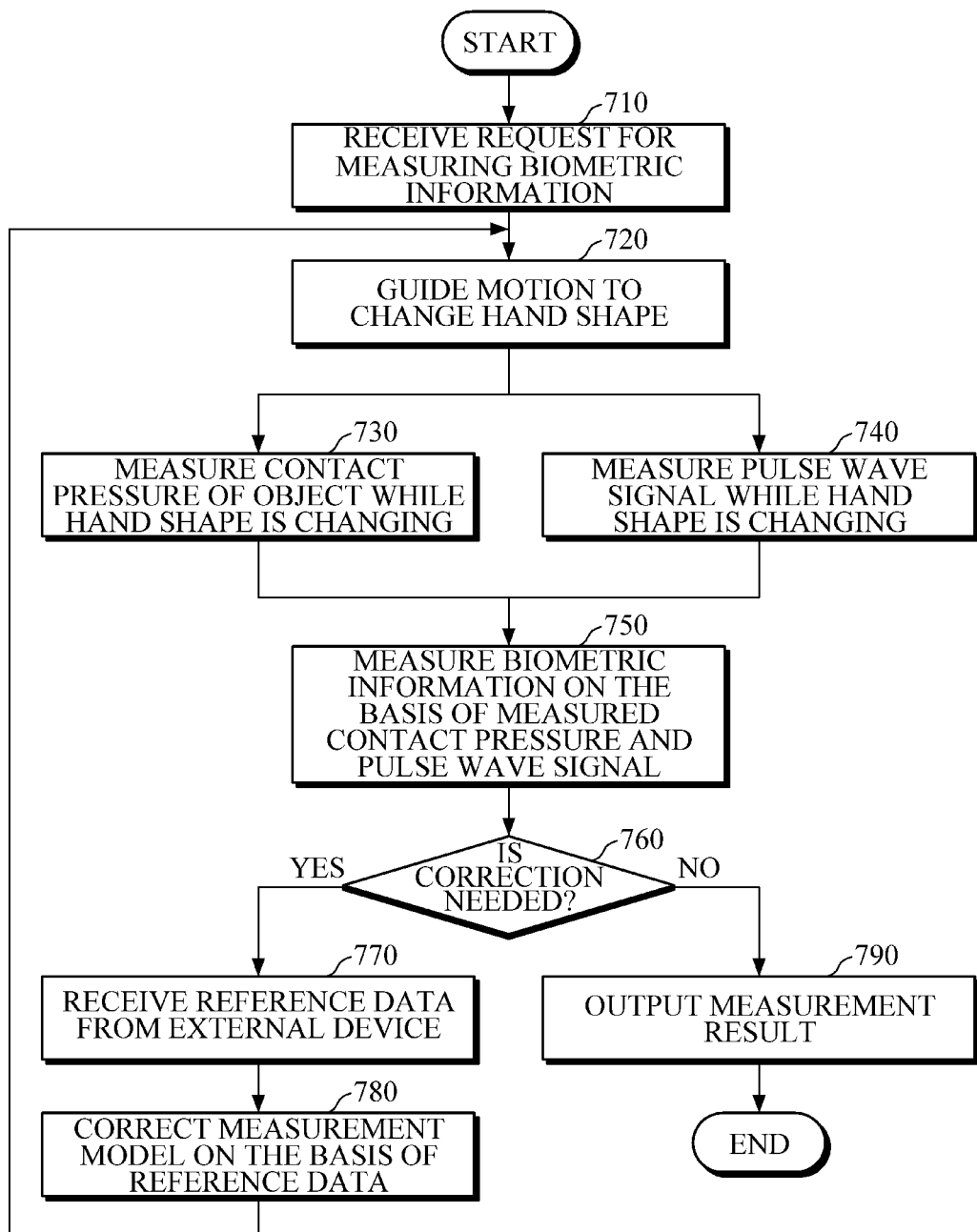
FIG. 7 is a flowchart illustrating a method of measuring biometric information according to an exemplary embodiment.

FIG. 7 is a flowchart illustrating a method of measuring biometric information according to an exemplary embodiment.

FIG. 7 illustrates an exemplary embodiment of a method of measuring biometric information which is performed by the apparatus 600 for measuring biometric information of FIG. 6, and the embodiment will be described in brief.

The apparatus 600 for measuring biometric information receives a request for measuring biometric information, as depicted in 710. At this time, the request may be received from the user. However, aspects of the present disclosure are not limited thereto, such that a processor may automatically generate a biometric information measurement request control signal when a pre-set criterion is satisfied, for example, at a predetermined interval or when a biometric information measurement result does not meet a predetermined criterion.

Then, the apparatus 600 guides the user in a motion to change a hand shape of the user in order to change a pressure applied to an object on which the main body is placed, as depicted in 720. In this case, the motion to change the hand shape is as described above.

Then, the apparatus 600 measures a contact pressure of the object while the hand shape is changing, as depicted in 730, and concurrently, measures a pulse wave signal of the object, as depicted in 740. For example, as the hand shape is continuously changed, the thickness of a wrist is changed, resulting in a change in tension of the strap wrapping around the wrist, and the contact pressure of the object which is changed by the tension of the strap is transmitted to the main body and may be measured by the contact pressure sensor. In addition, as the thickness of the wrist is changed, a degree to which the main body is attached to the wrist is changed, and thus the envelope of the pulse wave signal measured at a capillary or venous blood vessel in the upper wrist may also be changed.

Then, the biometric information is measured on the basis of the measured contact pressure and pulse wave signal. For example, as described above with reference to FIGS. 4A to 4E, systolic blood pressure, diastolic blood pressure, and the like may be measured on the basis of the oscillometric method.

Thereafter, whether to correct a biometric information measurement model is determined based on the biometric information measurement result, as depicted in 760. For example, even for the same user, the value of biometric information measured at each time of measurement may vary depending on the user's age, health status and the state change of the region to be examined according to the exercise. Therefore, criteria for correction, such as a normal range of a biometric information measurement value, for example, measured blood pressure, and the number of times that a measured value is out of the normal range, may be set in advance, and the apparatus 600 may determine whether to correct the biometric information measurement model by checking the correction criteria. When the blood pressure measured during a predetermined period is out of the normal range or the blood pressure measured during a predetermined period is out of the normal range more than a predetermined number of times, the apparatus 600 may determine that correction of the biometric information measurement model is needed.

Then, when it is determined in 760 that the biometric information measurement model needs to be corrected, the apparatus 600 may establish a connection with an external device and receive reference data from the external device, as depicted in 770. In this case, the reference data may be a cuff-pressure and user's cuff blood pressure measured by use of a cuff-type blood pressure measuring device.

Then, when the reference data is received from the external device, the biometric information measurement model is corrected, as depicted in 780.

Once the biometric information measurement model is corrected, operation 720 to guide the user for a motion to change the hand shape and the following operations are performed in order to re-measure biometric information using the corrected biometric information measurement model.

Then, when the biometric information is measured in operation 750 and it is determined in operation 760 that the correction of the biometric information measurement model is not needed, the biometric information measurement result is output to the user, as depicted in 790.

Figure 8:
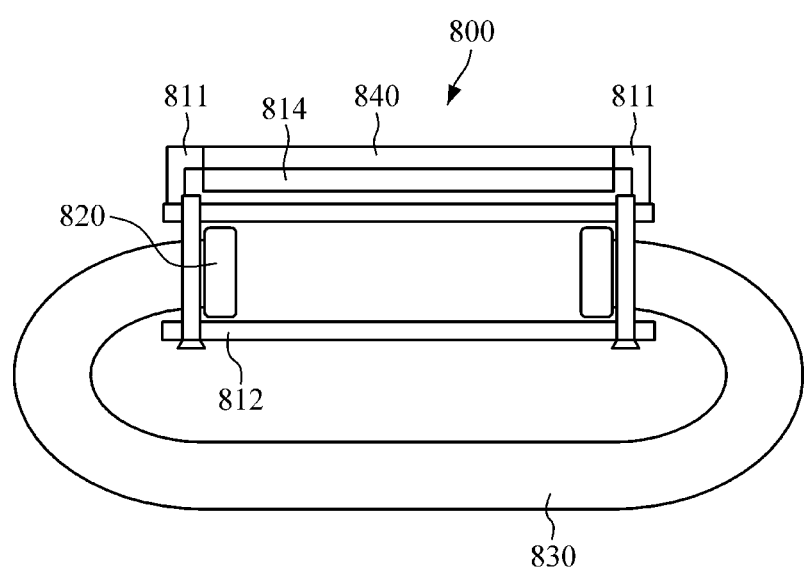
FIG. 8 is a diagram illustrating a configuration of an apparatus for measuring biometric information according to an exemplary embodiment.

FIG. 8 is a diagram illustrating a configuration of an apparatus for measuring biometric information according to an exemplary embodiment. The apparatus for measuring biometric information of the present embodiment may be a wristband-type wearable device.

Referring to FIG. 8, the apparatus for measuring biometric information according to an exemplary embodiment includes a main body 800 and a strap 830 configured to secure the main body 800 to an object while wrapping around the object.

The main body 800 may include a housing 812 and a main board 814 supported by a cover 811.

The strap 830 may be of a cuff-type in which air is injected so as to perform a similar function to a cuff of a cuff-type blood pressure measuring device. In this case, the strap 830 may be manufactured such that an air bag in which air is injected is mounted therein. One end of the strap 830 may be connected to the housing 812 of the main body 800 and the other end of the strap may be connected to a pressure sensor 820 mounted inside the housing 812. Alternatively, two pressure sensors 820 may be mounted inside the housing 812 and each end of the strap 830 may be connected to one of the pressure sensors 820.

The pressure sensor 820 may be mounted inside the housing 810 of the main body 800 as illustrated, and may be electrically connected to the main board 814. The pressure sensor 820 connected to one end of the strap 830 may measure a change in pressure applied to the object by the strap 830 with air injected therein according to the change of the hand shape. However, aspects of the present disclosure are not limited thereto, such that the pressure sensor 820 may be mounted on an outer surface of the strap 812 which comes in contact with a surface of a wrist under which the radial artery passes. The pressure sensor 820 may measure a change in pressure and convert it into an electrical pressure signal. In this case, the change in pressure detected in the wrist area may be a pulse wave and may include both an alternating current (AC) component and a direct current (DC) component. The pressure sensor 820 may be a piezoresistive pressure sensor or a capacitive pressure sensor capable of measuring a change in pressure detected in the wrist area, but is not limited thereto.

The main board 814 is supported by the cover 811 and may include a display 840 mounted on one surface thereof to visually display a variety of information. In addition, a speaker module or a haptic module capable of outputting information non-visually may be mounted in the main board 814. Also, a processor configured to execute an algorithm for biometric information measurement or to control various modules may be mounted in the main board 814.

The processor may guide the user by displaying, in the display 840, a motion to instruct the user to change the hand shape in order to change the pressure of the object to be inspected. When the pressure sensor 820 measures a pressure signal of the object while the user is changing the hand shape, the processor may measure biometric information by processing the measured pressure signal.

Figure 9:
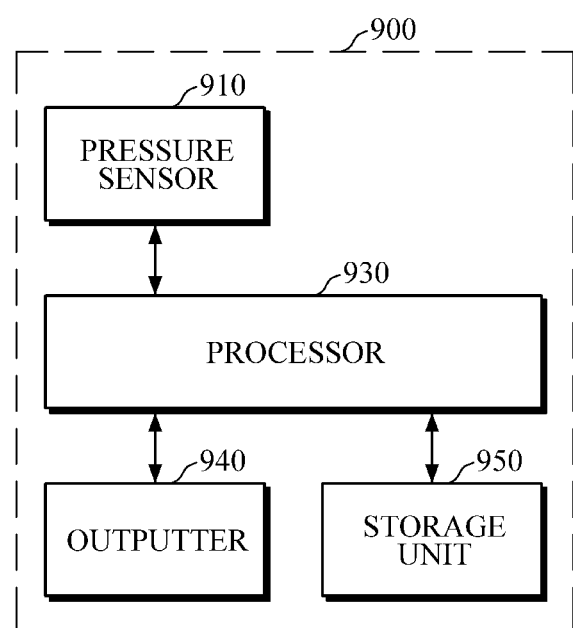
FIG. 9 is a block diagram illustrating an apparatus for measuring biometric information according to an exemplary embodiment.

FIG. 9 is a block diagram illustrating the apparatus for measuring biometric information according to an exemplary embodiment. Referring to FIG. 9, an apparatus 900 for measuring biometric information includes a pressure sensor 910, a processor 930, an outputter 940, and a storage unit 950.

The processor 930 may provide an interface to the user through the outputter 940, and process various control commands input by the user through the interface. For example, when the user inputs a request for measuring biometric information through the interface, the processor 930 may guide the user in a motion to change the hand shape by referencing the storage unit 950 in which a variety of information is stored. In addition, the processor 930 may generate a control signal for operating the pressure sensor 910 and may transmit the control signal to the pressure sensor 910.

The processor 930 may receive the measured pressure signal from the pressure sensor 910 and process the received pressure signal. For example, the processor 930 may process the pressure signal to extract a pressure value and a pulse wave signal therefrom. When the pressure signal is received, the processor 930 may pass the pressure signal through a low pass filter (LPF) and extract a change in pressure over time. In addition, the processor 930 may pass the pressure signal through a bandpass filter (BPF) to extract a pulse wave signal from which high frequency noise and baseline variation are removed.

When the pressure value and the pulse wave signal are extracted from the pressure signal, the processor 930 may measure biometric information using the extracted pressure value and pulse wave signal. For example, the processor 930 may measure blood pressure using an oscillometric method. When the biometric information is measured, the processor 930 may use the measurement result to determine whether the user's current health status or the measurement result is abnormal.

The outputter 940 may output the measured pressure signal or the biometric information measurement result under the control of the processor 930. In addition, according to the determination result of the processor 930, the outputter 940 may output warning information or alarm information to the user. In this case, the warning information or the alarm information may be visually provided using various colors, or may be provided through a non-visual method, such as voice, vibration, or tactile sensation.

The exemplary embodiments described above can be implemented as computer readable codes stored in a computer readable recording medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A wearable device for measuring biometric information, comprising:
   a main body configured to be worn on a user to be examined, wherein the main body comprises:
   a display configured to display guidance information instructing the user to increase or decrease a contact pressure exerted on a contact pressure sensor;
   the contact pressure sensor configured to measure the contact pressure exerted on the contact pressure sensor while the display is displaying the guidance information;
   a pulse wave sensor configured to measure a pulse wave signal of the user while the display is displaying the guidance information and the contact pressure sensor is measuring the contact pressure exerted on the contact pressure sensor; and
   a processor configured to obtain blood pressure information of the user based on a change of the pulse wave signal in relation to a change of the contact pressure that occurs while the display is displaying the guidance information,
   wherein the guidance information is configured to instruct the user to change a hand shape of the user, and
   wherein the processor is further configured to determine a relationship between the pulse wave signal and the contact pressure, identify a value of the contact pressure corresponding to a maximum peak value of the pulse wave signal based on the relationship between the pulse wave signal and the contact pressure, and obtain the blood pressure information based on the maximum peak value of the pulse wave signal and the value of the contact pressure corresponding to the maximum peak value of the pulse wave signal.

2. The wearable device of claim 1,
   wherein the main body comprises a first end and a second end;
   wherein the wearable device further comprises a strap comprising a first end connected to the first end of the main body and a second end connected to the second end of the main body; and
   wherein the strap is configured to wrap around the user and to hold the main body in a position in which the main body contacts the user.

3. The wearable device of claim 1, wherein the contact pressure sensor comprises at least one of a force sensor and a strain gauge.

4. The wearable device of claim 1, wherein the pulse wave sensor comprises at least one light source configured to emit light to the user and at least one detector configured to detect light emitted by the at least one light source and reflected from the user.

5. The wearable device of claim 4, wherein the at least one light source comprises at least one of a light emitting diode (LED), a laser diode, and a fluorescent body.

6. The wearable device of claim 1, wherein the guidance information is further configured to instruct the user to change the hand shape of the user upon receipt of a request for measuring the blood pressure information.

7. The wearable device of claim 6, wherein the change of the hand shape comprises at least one of a extending at least one finger from a fist, moving from a state in which the at least one finger is unfolded into a state of making the fist, sequentially opening each finger from the fist, and sequentially curling stretched fingers of an open hand, one by one, into the fist.

8. The wearable device of claim 6, wherein the change of the hand shape comprises at least one of bending a wrist in one direction in a state of holding a fist, bending the wrist in one direction in a state of keeping at least one finger unfolded, squeezing fingers while holding the fist, stretching at least two unfolded fingers apart from each other, bending a palm downward with all fingers open, bending the palm backward with all fingers open, and pressing the main body with a hand on which the main body is not worn.

9. The wearable device of claim 6, wherein the display is configured to output a measurement result upon measurement of the blood pressure information by the processor.

10. The wearable device of claim 1, wherein the main body further comprises a storage configured to store at least one of the guidance information for a motion to change the hand shape of the user and a measurement result of the blood pressure information.

11. The wearable device of claim 1, wherein the processor is further configured to extract feature points based on the measured pulse wave signal and a contact pressure signal and to determine the blood pressure information based on the feature points and a measurement model.

12. A wearable device for measuring biometric information, comprising:
  a main body configured to be worn on a user to be examined, wherein the main body comprises:
    a display configured to display guidance information instructing the user to increase or decrease a contact pressure exerted on a contact pressure sensor;
    the contact pressure sensor configured to measure the contact pressure exerted on the contact pressure sensor by the user while the display is displaying the guidance information;
    a pulse wave sensor configured to measure a pulse wave signal of the user while the display is displaying the guidance information; and
    a processor configured to measure the pulse wave signal and the contact pressure at a same time, determine a relationship between the pulse wave signal and the contact pressure, identify a value of the contact pressure corresponding to a maximum peak value of the pulse wave signal based on the relationship between the pulse wave signal and the contact pressure, and determine biometric information based on the maximum peak value of the pulse wave signal and the value of the contact pressure corresponding to the maximum peak value of the pulse wave signal.

13. The wearable device of claim 11, wherein the blood pressure information comprises at least one of systolic blood pressure, diastolic blood pressure, vascular age, arterial stiffness, aortic artery pressure waveform, vascular elasticity, stress index, and fatigue level.

14. A method of determining biometric information by a wearable device, the method comprising:
  display guidance information instructing a user of the wearable device to increase or decrease a contact pressure exerted on a contact pressure sensor;
  measuring the contact pressure exerted on the contact pressure sensor while displaying the guidance information;
  measuring a pulse wave signal of the user while displaying the guidance information and measuring the contact pressure exerted on the contact pressure sensor;
  obtaining blood pressure information of the user based on a change of the pulse wave signal in relation to a change of the contact pressure that occurs while displaying the guidance information;
  determining a relationship between the pulse wave signal and the contact pressure;
  identify a value of the contact pressure corresponding to a maximum peak value of the pulse wave signal based on the relationship between the pulse wave signal and the contact pressure; and
  obtaining the blood pressure information based on the maximum peak value of the pulse wave signal and the value of the contact pressure corresponding to the maximum peak value of the pulse wave signal.

15. The method of claim 14, further comprising:
  receiving a request for measuring the blood pressure information; and
  outputting the guidance information instructing a change of a hand shape upon receipt of the request for measuring the blood pressure information.

16. The method of claim 15, wherein the change of the hand shape comprises at least one of extending at least one finger from a fist, moving from a state in which at least one finger is unfolded into a state of making the fist, sequentially opening each finger from the fist, and sequentially curling stretched fingers of an open hand, one by one, into the fist.

17. The method of claim 15, wherein the change of the hand shape comprises at least one of bending a wrist in one direction in a state of holding a fist, bending the wrist in one direction in a state of keeping at least one finger unfolded, squeezing fingers while holding the fist, stretching at least two unfolded fingers to be apart from each other, bending a palm downward with all fingers open, bending the palm backward with all fingers open, and pressing the wearable device with a hand on which the wearable device is not worn.

18. The method of claim 14, further comprising outputting a measurement result upon determination of the blood pressure information.

19. The method of claim 14, wherein the determining the blood pressure information comprises extracting feature points based on the pulse wave signal and the contact pressure and determining the blood pressure information based on the feature points and a measurement model.

20. The wearable device of claim 1, wherein the processor is further configured to monitor first measurement values of the pulse wave signal that change at a same time while monitoring second measurement values of the contact pressure, and determine blood pressure of the user based on a function indicating a relation between the first measurement values of the pulse wave signal and the second measurement values of the contact pressure.

* * * * *